US005286486A

United States Patent [19]

Payne et al.

[11] Patent Number: 5,286,486

[45] Date of Patent: Feb. 15, 1994

[54] **COLEOPTERAN-ACTIVE *BACILLUS THURINGIENSIS* ISOLATES AND GENES ENCODING COLEOPTERAN-ACTIVE TOXINS**

[75] Inventors: Jewel M. Payne; Jenny M. Fu, both of San Diego, Calif.

[73] Assignee: Mycogen Corporation, San Diego, Calif.

[21] Appl. No.: 973,320

[22] Filed: Nov. 6, 1992

Related U.S. Application Data

[63] Continuation-in-part of Ser. No. 788,638, Nov. 6, 1991.

[51] Int. Cl.$^5$ .......... C12P 21/06; C12N 15/00; C07H 15/00

[52] U.S. Cl. .......... 424/93 L; 435/252.3; 536/23.71

[58] Field of Search .......... 424/93, 94.6; 435/252.5, 320.1; 536/27

[56] References Cited

U.S. PATENT DOCUMENTS

| | | | |
|---|---|---|---|
| 4,448,885 | 5/1984 | Schnepf et al. | 435/253 |
| 4,467,036 | 8/1984 | Schnepf et al. | 435/317 |
| 4,853,331 | 8/1989 | Herrnstadt et al. | 435/252.1 |
| 4,966,765 | 10/1990 | Payne | 424/93 |
| 4,996,155 | 2/1991 | Sick et al. | 435/252.3 |

FOREIGN PATENT DOCUMENTS

| | | |
|---|---|---|
| 0382990 | 2/1989 | European Pat. Off. . |
| 0501650 | 2/1992 | European Pat. Off. . |
| 9013651 | 11/1990 | PCT Int'l Appl. . |
| 9116433 | 10/1991 | PCT Int'l Appl. . |

OTHER PUBLICATIONS

Lecadet et al. J. Invert Path vol. 49 pp. 37–48 (1987).

Hofte et al. Microbial Reviews vol. 53 (2) pp. 242–255 (1989).

Perfontaine et al. App and Envir Microb vol. 53(12) 2808–2814.

Gaertner, Frank, and Leo Kim (1988) "Current Applied Recombinant DNA Projects" TIBTECH 6(4):S4–S7.

Gaertner, Frank (1990) "Cellular delivery systems for insecticidal proteins: living and non-living microorganisms" Controlled Delivery of Crop-Protection Agents, R. M. Wilkins, ed., Taylor and Francis, New York and London, 1990, pp. 245–255.

Couch, Terry L. (1980) "Mosquito Pathogenicity of *Bacillus thuringiensis* var. israelensis" Developments in Industrial Microbiology 22:61–76.

Beegle, Clayton C. (1978) "Use of Entomogenous Bacteria in Agroccosystems" Developments in Industrial Microbiology 20:97–104.

Krieg, Von A., A. M. Huger, G. A. Langenbruch, and W. Schnetter (1983) "*Bacillus thuringiensis* var tenebrionis: ein neuer, gegenuber Larven von Coleopteran wirksamer Pathotyp" Z. ang. Ent. 96:500–508.

Hofte, Herman, and H. R. Whiteley (1989) "Insecticidal Crystal Proteins of *Bacillus thuringiensis*" *Microbiological Reviews* 53(2):242–255.

Feitelson, Jerald S., Jewel Payne, and Leo Kim (1992) "*Bacillus thuringiensis: Insects and Beyond*" *Bio/Technology* 10:271–275.

Schnepf, H. Ernest, and H. R. Whiteley (1981) "Cloning and expression of the *Bacillus thuringiensis* crystal protein gene in *Escherichia coli*" *Proc. Natl. Acad. Sci. USA* 78(5):2893–2897.

*Primary Examiner*—Robert A. Wax
*Assistant Examiner*—D. Schmickel
*Attorney, Agent, or Firm*—Saliwanchik & Saliwanchik

[57] ABSTRACT

Certain known and available strains of *Bacillus thuringiensis* (*B.t.*) have been found to have activity against coleopteran pests. Previously, these strains were not known to have any insecticidal properties. The *B.t.* strains can be used in various environments to control coleopteran pests, e.g., the Colorado Potato Beetle. Also described are novel toxins, and genes coding for these toxins, which have coleopteran activity.

11 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 3414 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Bacillus thuringiensis
( B ) STRAIN: dakota
( C ) INDIVIDUAL ISOLATE: HD511

( v i i ) IMMEDIATE SOURCE:
( A ) LIBRARY: Lamdagem (TM)-11 library of J.M. Fu
( B ) CLONE: 511

( x i ) SEQUENCE DESCRIPTION: SEQ ID NO:1:

```
ATGAATTTAA ATAATTTAGG TGGATATGAA GATAGTAATA GAACATTAAA TAATTCTCTC    60
AATTATCCTA CTCAAAAAGC ATTATCACCA TCATTAAAGA ATATGAACTA CCAGGATTTT   120
TTATCTATAA CTGAGAGGGA ACAACCTGAA GCACTCGCTA GTGGTAATAC AGCTATTAAT   180
ACTGTAGTTA GTGTTACAGG GGCTACACTA AGTGCATTAG GTGTCCCAGG TGCAAGTTTT   240
ATCACTAACT TTTACCTGAA AATTACAGGC CTTTTATGGC CGCACAATAA AAATATTTGG   300
GATGAATTTA TGACAGAAGT AGAAACACTT ATTGAACAAA AAATAGAACA ATATGCAAGG   360
AATAAAGCAC TTGCAGAATT AGAGGGATTA GGAAATAACT TAACAATATA TCAACAGGCA   420
CTTGAAGATT GGCTGAACAA TCCTGATGAT CCAGCAACTA TAACACGAGT GATAGATCGT   480
TTTCGTATAT TAGATGCTTT ATTTGAATCA TATATGCCGT CATTTAGGGT TGCTGGATAT   540
GAAATACCAT TACTAACAGT TTACGCACAA GCGGCAAACC TTCATCTAGC TTTATTAAGA   600
GATTCTACTC TTTATGGAGA TAAATGGGGA TTCACTCAGA ACAACATTGA GGAAAATTAT   660
AATCGTCAAA AGAAACATAT CTCTGAATAT TCTAACCATT GCGTTAAGTG GTATAATAGT   720
GGTCTTAGCA GATTGAACGG TTCCACTTAT GAACAATGGA TAAATTATAA TCGTTTTCGT   780
AGAGAAATGA TATTAATGGT ATTAGATATT GCTGCTGTAT TTCCTATTTA TGACCCTCGA   840
ATGTATTCAA TGGAAACAAG TACGCAGTTA ACGAGAGAAG TGTATACCGA TCCAATTAGC   900
TTGTCAATTA GCAATCCAGA TATAGGTCCA AGTTTTTCTC AGATGGAAAA TACTGCGTTT   960
AGAACACCAC ACCTTGTTGA TTATTTAGAT GAGCTTTATA TATATACATC AAAATATAAA  1020
GCATTTTCAC ATGAGATTCA ACCAGACCTA TTTTATTGGT GTGTACATAA GGTTAGCTTT  1080
```

-continued

```
AAAAAATCGG AGCAATCCAA TTTATATACA ACAGGCATAT ATGGTAAAAC AAGTGGATAT 1140
ATTTCATCAG GAGCATATTC ATTTAGAGGG AATGATATCT ATAGAACATT AGCAGCTCCA 1200
TCAGTTGTAG TTTATCCGTA TACTCAGAAT TATGGTGTCG AGCAAGTTGA GTTTTACGGT 1260
GTAAAAGGGC ATGTACATTA TAGAGGAGAT AACAAATATG ATCTGACGTA TGATTCTATT 1320
GATCAATTAC CCCCAGACGG AGAACCAATA CACGAAAAAT ACACTCATCG ATTATGTCAT 1380
GCTACAGCTA TATCTAAATC AACTCCGGAT TATGATAATG CTACTATCCC GATCTTTTCT 1440
TGGACGCATA GAAGTGCGGA GTATTACAAT AGAATCTATC CAAACAAAAT CAAAAAAATT 1500
CCAGCTGTAA AAATGTATAA ACTAGATGAT CTATCTACAG TTGTCAAAGG GCCTGGATTT 1560
ACAGGTGGAG ATTTAGTTAA GAGAGGGAGT AATGGTTATA TAGGAGATAT AAAGGCTACC 1620
GTAAACTCAC CACTTTCTCA AAAATATCGT GTTAGAGTTC GATACGCCAC TAGTGTTTCT 1680
GGACTATTCA ACGTGTTTAT TAATGATGAA ATAGCGCTTC AAAAAAATTT TCAAAGTACT 1740
GTAGAAACAA TAGGTGAAGG AAAAGATTTA ACCTATGGTT CATTTGGATA TATAGAATAT 1800
TCTACGACCA TTCAATTTCC GAATGAGCAT CCAAAAATCA CTCTTCATTT AAACCATTTG 1860
AGTAACAATT CACCATTTTA TGTAGATTCA ATCGAATTTA TCCCTGTAGA TGTAAATTAT 1920
GATGAAAAAG AAAAACTAGA AAAAGCACAG AAAGCCGTGA ATACCTTGTT TACAGAGGGA 1980
AGAAATGCAC TCCAAAAATA CGTGACAGAT TATAAAGTGG ACCAGGTTTC AATTTTAGTG 2040
GATTGTATAT CAGGGGATTT ATATCCCAAT GAGAAACGCG AACTACAAAA TCTAGTCAAA 2100
TACGCAAAAC GTTTGAGCTA TTCCCGTAAT TTACTTCTAG ATCCCACATT CGATTCTATT 2160
AATTCATCTG AGGAGAATGG TTGGTATGGA AGTAATGGTA TTGTGATTGG AAATGGGGAT 2220
TTTGTATTCA AAGGTAACTA TTTAATTTTT TCAGGTACCA ATGATACACA ATATCCAACA 2280
TATCTCTACC AAAAAATAGA TGAATCCAAA CTCAAAGAAT ATTCACGCTA TAAACTGAAA 2340
GGTTTTATCG AAAGTAGTCA GGATTTAGAA GCTTATGTGA TTCGCTATGA TGCAAAACAT 2400
AGAACATTGG ATGTTTCTGA TAATCTATTA CCAGATATTC TCCCTGAGAA TACATGTGGA 2460
GAACCAAATC GCTGCGCGGC ACAACAATAC CTGGATGAAA ATCCAAGTTC AGAATGTAGT 2520
TCGATGCAAG ATGGAATTTT GTCTGATTCG CATTCATTTT CTCTTAATAT AGATACAGGT 2580
TCTATCAATC ACAATGAGAA TTTAGGAATT TGGGTGTTGT TTAAAATTTC GACATTAGAA 2640
GGATATGCGA AATTTGGAAA TCTAGAAGTG ATTGAAGATG GCCCAGTTAT TGGAGAAGCA 2700
TTAGCCCGTG TGAAGCGCCA AGAAACGAAG TGGAGAAACA AGTTAGCCCA AATGACAACG 2760
GAAACACAAG CGATTTATAC ACGAGCAAAA CAAGCGCTGG ATAATCTTTT TGCGAATGCA 2820
CAAGACTCTC ACTTAAAAAT AGATGTTACA TTTGCGGAAA TTGCGGCTGC AAGAAAGATT 2880
GTCCAATCAA TACGCGAAGT GTATATGTCA TGGTTATCTG TTGTTCCAGG TGTAAATCAC 2940
CCTATTTTTA CAGAGTTAAG TGGGAGAGTA CAACGAGCAT TTCAATTATA TGATGTACGA 3000
AATGTTGTGC GTAATGGTCG ATTCCTCAAT GGCTTATCCG ATTGGATTGT AACATCTGAC 3060
GTAAACGTAC AAGAAGAAAA TGGGAATAAC GTATTAGTTC TTAACAATTG GGATGCGCAA 3120
GTATTACGAA ACGTAAAACT CTATCAAGAC CGTGGGTATG TCTTACGTGT AACAGCGCGC 3180
AAGATAGGAA TTGGGGAAGG ATATATAACG ATTACTGATG AAGAAGGGCA TACAGATCAA 3240
TTGAGATTTA CTGCATGTGA AGAGATTGAT GCATCTAATG CGTTTATATC CGGTTATATT 3300
ACAAAAGAAC TGGAATTCTT CCCAGATACA GAGAAAGTGC ATATAGAAAT AGGCGAAACA 3360
GAAGGAATAT TCCTGGTAGA AAGTATAGAG TTATTTTTGA TGGAAGAGCT ATGT 3414
```

(2) INFORMATION FOR SEQ ID NO:2:

-continued ( i ) SEQUENCE CHARACTERISTICS:
( A ) LENGTH: 1138 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: Bacillus thuringiensis
( B ) STRAIN: dakota
( C ) INDIVIDUAL ISOLATE: HD511

( v i i ) IMMEDIATE SOURCE:
( A ) LIBRARY: Lamdagem (TM)-11 library of J.M. Fu
( B ) CLONE: 511

( x i ) SEQUENCE DESCRIPTION: SEQ ID NO:2:

Met Asn Leu Asn Asn Leu Gly Gly Tyr Glu Asp Ser Asn Arg Thr Leu
1 5 10 15

Asn Asn Ser Leu Asn Tyr Pro Thr Gln Lys Ala Leu Ser Pro Ser Leu
20 25 30

Lys Asn Met Asn Tyr Gln Asp Phe Leu Ser Ile Thr Glu Arg Glu Gln
35 40 45

Pro Glu Ala Leu Ala Ser Gly Asn Thr Ala Ile Asn Thr Val Val Ser
50 55 60

Val Thr Gly Ala Thr Leu Ser Ala Leu Gly Val Pro Gly Ala Ser Phe
65 70 75 80

Ile Thr Asn Phe Tyr Leu Lys Ile Thr Gly Leu Leu Trp Pro His Asn
85 90 95

Lys Asn Ile Trp Asp Glu Phe Met Thr Glu Val Glu Thr Leu Ile Glu
100 105 110

Gln Lys Ile Glu Gln Tyr Ala Arg Asn Lys Ala Leu Ala Glu Leu Glu
115 120 125

Gly Leu Gly Asn Asn Leu Thr Ile Tyr Gln Gln Ala Leu Glu Asp Trp
130 135 140

Leu Asn Asn Pro Asp Asp Pro Ala Thr Ile Thr Arg Val Ile Asp Arg
145 150 155 160

Phe Arg Ile Leu Asp Ala Leu Phe Glu Ser Tyr Met Pro Ser Phe Arg
165 170 175

Val Ala Gly Tyr Glu Ile Pro Leu Leu Thr Val Tyr Ala Gln Ala Ala
180 185 190

Asn Leu His Leu Ala Leu Leu Arg Asp Ser Thr Leu Tyr Gly Asp Lys
195 200 205

Trp Gly Phe Thr Gln Asn Asn Ile Glu Glu Asn Tyr Asn Arg Gln Lys
210 215 220

Lys His Ile Ser Glu Tyr Ser Asn His Cys Val Lys Trp Tyr Asn Ser
225 230 235 240

Gly Leu Ser Arg Leu Asn Gly Ser Thr Tyr Glu Gln Trp Ile Asn Tyr
245 250 255

Asn Arg Phe Arg Arg Glu Met Ile Leu Met Val Leu Asp Ile Ala Ala
260 265 270

Val Phe Pro Ile Tyr Asp Pro Arg Met Tyr Ser Met Glu Thr Ser Thr
275 280 285

Gln Leu Thr Arg Glu Val Tyr Thr Asp Pro Ile Ser Leu Ser Ile Ser
290 295 300

Asn Pro Asp Ile Gly Pro Ser Phe Ser Gln Met Glu Asn Thr Ala Phe
305 310 315 320

-continued

| | | | | | | | | | | | | | | | |
|---|---|---|---|---|---|---|---|---|---|---|---|---|---|---|---|
| Arg | Thr | Pro | His | Leu | Val | Asp | Tyr | Leu | Asp | Glu | Leu | Tyr | Ile | Tyr | Thr |
| | | | | 325 | | | | | 330 | | | | | 335 | |
| Ser | Lys | Tyr | Lys | Ala | Phe | Ser | His | Glu | Ile | Gln | Pro | Asp | Leu | Phe | Tyr |
| | | | 340 | | | | | 345 | | | | | 350 | | |
| Trp | Cys | Val | His | Lys | Val | Ser | Phe | Lys | Lys | Ser | Glu | Gln | Ser | Asn | Leu |
| | | 355 | | | | | 360 | | | | | 365 | | | |
| Tyr | Thr | Thr | Gly | Ile | Tyr | Gly | Lys | Thr | Ser | Gly | Tyr | Ile | Ser | Ser | Gly |
| | 370 | | | | | 375 | | | | | 380 | | | | |
| Ala | Tyr | Ser | Phe | Arg | Gly | Asn | Asp | Ile | Tyr | Arg | Thr | Leu | Ala | Ala | Pro |
| 385 | | | | | 390 | | | | | 395 | | | | | 400 |
| Ser | Val | Val | Val | Tyr | Pro | Tyr | Thr | Gln | Asn | Tyr | Gly | Val | Glu | Gln | Val |
| | | | | 405 | | | | | 410 | | | | | 415 | |
| Glu | Phe | Tyr | Gly | Val | Lys | Gly | His | Val | His | Tyr | Arg | Gly | Asp | Asn | Lys |
| | | | 420 | | | | | 425 | | | | | 430 | | |
| Tyr | Asp | Leu | Thr | Tyr | Asp | Ser | Ile | Asp | Gln | Leu | Pro | Pro | Asp | Gly | Glu |
| | | 435 | | | | | 440 | | | | | 445 | | | |
| Pro | Ile | His | Glu | Lys | Tyr | Thr | His | Arg | Leu | Cys | His | Ala | Thr | Ala | Ile |
| | 450 | | | | | 455 | | | | | 460 | | | | |
| Ser | Lys | Ser | Thr | Pro | Asp | Tyr | Asp | Asn | Ala | Thr | Ile | Pro | Ile | Phe | Ser |
| 465 | | | | | 470 | | | | | 475 | | | | | 480 |
| Trp | Thr | His | Arg | Ser | Ala | Glu | Tyr | Tyr | Asn | Arg | Ile | Tyr | Pro | Asn | Lys |
| | | | | 485 | | | | | 490 | | | | | 495 | |
| Ile | Lys | Lys | Ile | Pro | Ala | Val | Lys | Met | Tyr | Lys | Leu | Asp | Asp | Leu | Ser |
| | | | 500 | | | | | 505 | | | | | 510 | | |
| Thr | Val | Val | Lys | Gly | Pro | Gly | Phe | Thr | Gly | Gly | Asp | Leu | Val | Lys | Arg |
| | | 515 | | | | | 520 | | | | | 525 | | | |
| Gly | Ser | Asn | Gly | Tyr | Ile | Gly | Asp | Ile | Lys | Ala | Thr | Val | Asn | Ser | Pro |
| | 530 | | | | | 535 | | | | | 540 | | | | |
| Leu | Ser | Gln | Lys | Tyr | Arg | Val | Arg | Val | Arg | Tyr | Ala | Thr | Ser | Val | Ser |
| 545 | | | | | 550 | | | | | 555 | | | | | 560 |
| Gly | Leu | Phe | Asn | Val | Phe | Ile | Asn | Asp | Glu | Ile | Ala | Leu | Gln | Lys | Asn |
| | | | | 565 | | | | | 570 | | | | | 575 | |
| Phe | Gln | Ser | Thr | Val | Glu | Thr | Ile | Gly | Glu | Gly | Lys | Asp | Leu | Thr | Tyr |
| | | | 580 | | | | | 585 | | | | | 590 | | |
| Gly | Ser | Phe | Gly | Tyr | Ile | Glu | Tyr | Ser | Thr | Thr | Ile | Gln | Phe | Pro | Asn |
| | | 595 | | | | | 600 | | | | | 605 | | | |
| Glu | His | Pro | Lys | Ile | Thr | Leu | His | Leu | Asn | His | Leu | Ser | Asn | Asn | Ser |
| | 610 | | | | | 615 | | | | | 620 | | | | |
| Pro | Phe | Tyr | Val | Asp | Ser | Ile | Glu | Phe | Ile | Pro | Val | Asp | Val | Asn | Tyr |
| 625 | | | | | 630 | | | | | 635 | | | | | 640 |
| Asp | Glu | Lys | Glu | Lys | Leu | Glu | Lys | Ala | Gln | Lys | Ala | Val | Asn | Thr | Leu |
| | | | | 645 | | | | | 650 | | | | | 655 | |
| Phe | Thr | Glu | Gly | Arg | Asn | Ala | Leu | Gln | Lys | Tyr | Val | Thr | Asp | Tyr | Lys |
| | | | 660 | | | | | 665 | | | | | 670 | | |
| Val | Asp | Gln | Val | Ser | Ile | Leu | Val | Asp | Cys | Ile | Ser | Gly | Asp | Leu | Tyr |
| | | 675 | | | | | 680 | | | | | 685 | | | |
| Pro | Asn | Glu | Lys | Arg | Glu | Leu | Gln | Asn | Leu | Val | Lys | Tyr | Ala | Lys | Arg |
| | 690 | | | | | 695 | | | | | 700 | | | | |
| Leu | Ser | Tyr | Ser | Arg | Asn | Leu | Leu | Leu | Asp | Pro | Thr | Phe | Asp | Ser | Ile |
| 705 | | | | | 710 | | | | | 715 | | | | | 720 |
| Asn | Ser | Ser | Glu | Glu | Asn | Gly | Trp | Tyr | Gly | Ser | Asn | Gly | Ile | Val | Ile |
| | | | | 725 | | | | | 730 | | | | | 735 | |
| Gly | Asn | Gly | Asp | Phe | Val | Phe | Lys | Gly | Asn | Tyr | Leu | Ile | Phe | Ser | Gly |
| | | | 740 | | | | | 745 | | | | | 750 | | |

-continued

Thr Asn Asp Thr Gln Tyr Pro Thr Tyr Leu Tyr Gln Lys Ile Asp Glu
755 760 765

Ser Lys Leu Lys Glu Tyr Ser Arg Tyr Lys Leu Lys Gly Phe Ile Glu
770 775 780

Ser Ser Gln Asp Leu Glu Ala Tyr Val Ile Arg Tyr Asp Ala Lys His
785 790 795 800

Arg Thr Leu Asp Val Ser Asp Asn Leu Leu Pro Asp Ile Leu Pro Glu
805 810 815

Asn Thr Cys Gly Glu Pro Asn Arg Cys Ala Ala Gln Gln Tyr Leu Asp
820 825 830

Glu Asn Pro Ser Ser Glu Cys Ser Ser Met Gln Asp Gly Ile Leu Ser
835 840 845

Asp Ser His Ser Phe Ser Leu Asn Ile Asp Thr Gly Ser Ile Asn His
850 855 860

Asn Glu Asn Leu Gly Ile Trp Val Leu Phe Lys Ile Ser Thr Leu Glu
865 870 875 880

Gly Tyr Ala Lys Phe Gly Asn Leu Glu Val Ile Glu Asp Gly Pro Val
885 890 895

Ile Gly Glu Ala Leu Ala Arg Val Lys Arg Gln Glu Thr Lys Trp Arg
900 905 910

Asn Lys Leu Ala Gln Met Thr Thr Glu Thr Gln Ala Ile Tyr Thr Arg
915 920 925

Ala Lys Gln Ala Leu Asp Asn Leu Phe Ala Asn Ala Gln Asp Ser His
930 935 940

Leu Lys Ile Asp Val Thr Phe Ala Glu Ile Ala Ala Ala Arg Lys Ile
945 950 955 960

Val Gln Ser Ile Arg Glu Val Tyr Met Ser Trp Leu Ser Val Val Pro
965 970 975

Gly Val Asn His Pro Ile Phe Thr Glu Leu Ser Gly Arg Val Gln Arg
980 985 990

Ala Phe Gln Leu Tyr Asp Val Arg Asn Val Val Arg Asn Gly Arg Phe
995 1000 1005

Leu Asn Gly Leu Ser Asp Trp Ile Val Thr Ser Asp Val Asn Val Gln
1010 1015 1020

Glu Glu Asn Gly Asn Asn Val Leu Val Leu Asn Asn Trp Asp Ala Gln
1025 1030 1035 1040

Val Leu Arg Asn Val Lys Leu Tyr Gln Asp Arg Gly Tyr Val Leu Arg
1045 1050 1055

Val Thr Ala Arg Lys Ile Gly Ile Gly Glu Gly Tyr Ile Thr Ile Thr
1060 1065 1070

Asp Glu Glu Gly His Thr Asp Gln Leu Arg Phe Thr Ala Cys Glu Glu
1075 1080 1085

Ile Asp Ala Ser Asn Ala Phe Ile Ser Gly Tyr Ile Thr Lys Glu Leu
1090 1095 1100

Glu Phe Phe Pro Asp Thr Glu Lys Val His Ile Glu Ile Gly Glu Thr
1105 1110 1115 1120

Glu Gly Ile Phe Leu Val Glu Ser Ile Glu Leu Phe Leu Met Glu Glu
1125 1130 1135

Leu Cys ( 2 ) INFORMATION FOR SEQ ID NO:3:

( i ) SEQUENCE CHARACTERISTICS:
( A ) LENGTH: 3414 base pairs
( B ) TYPE: nucleic acid
( C ) STRANDEDNESS: double
( D ) TOPOLOGY: linear -continued ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Bacillus thuringiensis
( B ) STRAIN: kumamotoensis
( C ) INDIVIDUAL ISOLATE: HD867

( v i i ) IMMEDIATE SOURCE:
( A ) LIBRARY: Lamdagem (TM)-11 library of J.M. Fu
( B ) CLONE: 867

( x i ) SEQUENCE DESCRIPTION: SEQ ID NO:3:

ATGAATTTAA ATAATTTAGG TGGATATGAA GATAGTAATA GAACATTAAA TAATTCTCTC 60

AATTATCCTA CTCAAAAAGC ATTATCACCA TCATTAAAGA ATATGAACTA CCAGGATTTT 120

TTATCTATAA CTGAGAGGGA ACAGCCTGAA GCACTCGCTA GTGGTAATAC AGCTATTAAT 180

ACTGTAGTTA GTGTTACAGG GGCTACACTA AGTGCGTTAG GTGTCCCAGG TGCAAGTTTT 240

ATCACTAACT TTTACCTGAA AATTACAGGC CTTTTATGGC CACACGATAA AAATATTTGG 300

GATGAATTTA TGACAGAAGT AGAAACACTT ATTGAACAAA AAATAGAACA ATATGCAAGG 360

AATAAAGCAC TTGCAGAATT AGAGGGATTA GGAAATAACT TAACGATATA TCAACAGGCA 420

CTTGAAGATT GGCTGAACAA TCCTGATGAT CCAGCAACTA TAACACGAGT GATAGATCGT 480

TTTCGTATAT TAGATGCTTT ATTTGAATCA TATATGCCGT CATTTAGGGT TGCTGGATAT 540

GAAATACCAT TACTAACAGT TTACGCACAA GCGGCAAACC TTCATCTAGC TTTATTAAGA 600

GATTCTACTC TTTATGGAGA TAAATGGGAA TTCACTCAGA ACAACATTGA GGAAAATTAT 660

AATCGTCAAA AGAAACATAT TTCTGAATAT TCTAACCATT GCGTTAAGTG GTATAATAGT 720

GGTCTTAGCA GATTGAACGG TTCCACTTAT GAACAATGGA TAAATTATAA TCGTTTTCGT 780

AGAGAAATGA TATTAATGGT ATTAGATATT GCTGCTGTAT TTCCTATTTA TGACCCTCGA 840

ATGTATTCAA TGGAAACAAG TACGCAGTTA ACGAGAGAAG TGTATACCGA TCCAATTAGC 900

TTGTCAATTA GCAATCCAGG TATAGGTCCA AGTTTTTCTC AGATGGAAAA TACTGCGATT 960

AGAACACCAC ACCTTGTTGA TTATTTAGAT GAGCTTTATA TATATACATC AAAATATAAA 1020

GCATTTTCAC ATGAGATTCA ACCAGACCTA TTTTATTGGA GTGCACATAA GGTTAGCTTT 1080

AAACAATCGG AGCAATCCAA TTTATATACA ACAGGCATAT ATGGTAAAAC AAGTGGATAT 1140

ATTTCATCAG GGGCATATTC ATTTAGAGGT AATGATATCT ATAGAACATT AGCAGCTCCA 1200

TCAGTTGTAG TTTATCCGTA TACTCAGAAT TATGGTGTCG AGCAAGTTGA GTTTTACGGT 1260

GTAAAAGGGC ACGTACATTA TAGAGGAGAT AACAAATATG ATCTGACGTA TGATTCTATT 1320

GATCAATTAC CCCCAGACGG AGAACCAATA CACGAAAAAT ACACTCATCG ATTATGTCAT 1380

GCTACAGCTA TATCTAAATC AACTCCGGAT TATGATAATG CTACTATCCC GATCTTTTCT 1440

TGGACGCATA GAAGTGCGGA GTATTACAAT AGAATCTATC CAAACAAAAT CACAAAAATT 1500

CCAGCTGTAA AAATGTATAA ACTAGGTGAT ACATCTACAG TTGTCAAAGG GCCTGGATTT 1560

ACAGGTGGAG ATTTAGTTAA GAGAGGGAGT AATGGTTATA TAGGAGATAT AAAGGCTACC 1620

GTAAACTCAC CACTTTCTCA AAATTATCGT GTTAGAGTTC GATACGCCAC TAATGTTTCT 1680

GGACAATTCA ACGTGTATAT TAATGATAAA ATAACGCTTC AAAGAAAGTT TCAAAATACT 1740

GTAGAAACAA TAGGTGAAGG AAAAGATTTA ACCTATGGTT CATTTGGATA TATAGAATAT 1800

TCTACGACCA TTCAATTTCC GGATAAGCAT CCAAAAATCA CTCTTCATTT AAGTGATTTG 1860

AGTAACAATT CATCATTTTA TGTAGATTCA ATCGAATTTA TCCCTGTAGA TGTAAATTAT 1920

-continued

```
GATGAAAAAG AAAAACTAGA AAAAGCACAG AAAGCCGTGA ATACCTTGTT TACAGAGGGA   1980
AGAAATGCAC TCCAAAAAGA CGTGACAGAT TATAAAGTGG ACCAGGTTTC AATTTTAGTG   2040
GATTGTATAT CAGGGGATTT ATATCCCAAT GAGAAACGCG AACTACAAAA TCTAGTCAAA   2100
TACGCAAAAC GTTTGAGCTA TTCCCGTAAT TTACTTCTAG ATCCAACATT CGATTCTATT   2160
AATTCATCTG AGGAGAATGG TTGGTATGGA AGTAATGGTA TTGTGATTGG AAATGGGGAT   2220
TTTGTATTCA AAGGTAACTA TTTAATTTTT TCAGGTACCA ATGATACACA ATATCCAACA   2280
TATCTCTACC AAAAAATAGA TGAATCCAAA CTCAAAGAAT ATACACGCTA TAAACTGAAA   2340
GGTTTTATCG AAAGTAGTCA GGATTTAGAA GCTTATGTGA TTCGCTATGA TGCAAAACAT   2400
AGAACATTGG ATGTTTCTGA TAATCTATTA CCAGATATTC TCCCTGAGAA TACATGTGGA   2460
GAACCAAATC GCTGCGCGGC ACAACAATAC CTGGATGAAA ATCCAAGTTC AGAATGTAGT   2520
TCGATGCAAG ATGGAATTTT GTCTGATTCG CATTCATTTT CTCTTAATAT AGATATAGGT   2580
TCTATTAATC ACAATGAGAA TTTAGGAATT TGGGTGTTGT TTAAAATTTC GACACTAGAA   2640
GGATATGCGA AATTTGGAAA TCTAGAAGTG ATTGAAGATG GCCCAGTTAT TGGAGAAGCA   2700
TTAGCCCGTG TGAAACGCCA AGAAACGAAG TGGAGAAACA AGTTAGCCCA ACTGACAACG   2760
GAAACACAAG CGATTTATAC ACGAGCAAAA CAAGCGCTGG ATAATCTTTT TGCGAATGCA   2820
CAAGACTCTC ACTTAAAAAT AGATGTTACA TTTGCGGAAA TTGCGGCTGC AAGAAAGATT   2880
GTCCAATCAA TACGCGAAGC GTATATGTCA TGGTTATCTG TTGTTCCAGG TGTAAATCAC   2940
CCTATTTTTA CAGAGTTAAG TGAGCGAGTA CAACGAGCAT TTCAATTATA TGATGTACGA   3000
AATGTTGTGC GTAATGGTCG ATTCCTCAAT GGCTTATCCG ATTGGATTGT AACATCTGAC   3060
GTAAAGGTAC AAGAAGAAAA TGGGAATAAC GTATTAGTTC TTAACAATTG GGATGCACAA   3120
GTATTACAAA ACGTAAAACT CTATCAAGAC CGTGGGTATA TCTTACGTGT AACAGCGCGC   3180
AAGATAGGAA TTGGGGAAGG ATATATAACG ATTACGGATG AAGAAGGGCA TACAGTTCAA   3240
TTGAGATTTA CTGCATGTGA AGTGATTGAT GCATCTAATG CGTTTATATC CGGTTATATT   3300
ACAAAAGAAC TGGAATTCTT CCCAGATACA GAGAAAGTGC ATATAGAAAT AGGCGAAACA   3360
GAAGGAATAT TCCTGGTAGA AAGTATAGAG TTATTTTTGA TGGAAGAGCT ATGT         3414
```

( 2 ) INFORMATION FOR SEQ ID NO:4:

( i ) SEQUENCE CHARACTERISTICS:
( A ) LENGTH: 1138 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: Bacillus thuringiensis
( B ) STRAIN: kumamotoensis
( C ) INDIVIDUAL ISOLATE: HD867

( v i i ) IMMEDIATE SOURCE:
( A ) LIBRARY: Lamdagem (TM)-11 library of J.M. Fu
( B ) CLONE: 867

( x i ) SEQUENCE DESCRIPTION: SEQ ID NO:4:

```
Met Asn Leu Asn Asn Leu Gly Gly Tyr Glu Asp Ser Asn Arg Thr Leu
1               5                   10                  15

Asn Asn Ser Leu Asn Tyr Pro Thr Gln Lys Ala Leu Ser Pro Ser Leu
            20                  25                  30
```

-continued

```
Lys Asn Met Asn Tyr Gln Asp Phe Leu Ser Ile Thr Glu Arg Glu Gln
        35                  40                  45

Pro Glu Ala Leu Ala Ser Gly Asn Thr Ala Ile Asn Thr Val Val Ser
    50                  55                  60

Val Thr Gly Ala Thr Leu Ser Ala Leu Gly Val Pro Gly Ala Ser Phe
65                  70                  75                  80

Ile Thr Asn Phe Tyr Leu Lys Ile Thr Gly Leu Leu Trp Pro His Asn
                85                  90                  95

Lys Asn Ile Trp Asp Glu Phe Met Thr Glu Val Glu Thr Leu Ile Glu
            100                 105                 110

Gln Lys Ile Glu Gln Tyr Ala Arg Asn Lys Ala Leu Ala Glu Leu Glu
        115                 120                 125

Gly Leu Gly Asn Asn Leu Thr Ile Tyr Gln Gln Ala Leu Glu Asp Trp
    130                 135                 140

Leu Asn Asn Pro Asp Asp Pro Ala Thr Ile Thr Arg Val Ile Asp Arg
145                 150                 155                 160

Phe Arg Ile Leu Asp Ala Leu Phe Glu Ser Tyr Met Pro Ser Phe Arg
                165                 170                 175

Val Ala Gly Tyr Glu Ile Pro Leu Leu Thr Val Tyr Ala Gln Ala Ala
            180                 185                 190

Asn Leu His Leu Ala Leu Leu Arg Asp Ser Thr Leu Tyr Gly Asp Lys
        195                 200                 205

Trp Gly Phe Thr Gln Asn Asn Ile Glu Glu Asn Tyr Asn Arg Gln Lys
    210                 215                 220

Lys His Ile Ser Glu Tyr Ser Asn His Cys Val Lys Trp Tyr Asn Ser
225                 230                 235                 240

Gly Leu Ser Arg Leu Asn Gly Ser Thr Tyr Glu Gln Trp Ile Asn Tyr
                245                 250                 255

Asn Arg Phe Arg Arg Glu Met Ile Leu Met Val Leu Asp Ile Ala Ala
            260                 265                 270

Val Phe Pro Ile Tyr Asp Pro Arg Met Tyr Ser Met Glu Thr Ser Thr
        275                 280                 285

Gln Leu Thr Arg Glu Val Tyr Thr Asp Pro Ile Ser Leu Ser Ile Ser
    290                 295                 300

Asn Pro Asp Ile Gly Pro Ser Phe Ser Gln Met Glu Asn Thr Ala Phe
305                 310                 315                 320

Arg Thr Pro His Leu Val Asp Tyr Leu Asp Glu Leu Tyr Ile Tyr Thr
                325                 330                 335

Ser Lys Tyr Lys Ala Phe Ser His Glu Ile Gln Pro Asp Leu Phe Tyr
            340                 345                 350

Trp Cys Val His Lys Val Ser Phe Lys Lys Ser Glu Gln Ser Asn Leu
        355                 360                 365

Tyr Thr Thr Gly Ile Tyr Gly Lys Thr Ser Gly Tyr Ile Ser Ser Gly
    370                 375                 380

Ala Tyr Ser Phe Arg Gly Asn Asp Ile Tyr Arg Thr Leu Ala Ala Pro
385                 390                 395                 400

Ser Val Val Val Tyr Pro Tyr Thr Gln Asn Tyr Gly Val Glu Gln Val
                405                 410                 415

Glu Phe Tyr Gly Val Lys Gly His Val His Tyr Arg Gly Asp Asn Lys
            420                 425                 430

Tyr Asp Leu Thr Tyr Asp Ser Ile Asp Gln Leu Pro Pro Asp Gly Glu
        435                 440                 445

Pro Ile His Glu Lys Tyr Thr His Arg Leu Cys His Ala Thr Ala Ile
    450                 455                 460

Ser Lys Ser Thr Pro Asp Tyr Asp Asn Ala Thr Ile Pro Ile Phe Ser
```

-continued 465 470 475 480

Trp Thr His Arg Ser Ala Glu Tyr Tyr Asn Arg Ile Tyr Pro Asn Lys
485 490 495

Ile Lys Lys Ile Pro Ala Val Lys Met Tyr Lys Leu Asp Asp Leu Ser
500 505 510

Thr Val Val Lys Gly Pro Gly Phe Thr Gly Gly Asp Leu Val Lys Arg
515 520 525

Gly Ser Asn Gly Tyr Ile Gly Asp Ile Lys Ala Thr Val Asn Ser Pro
530 535 540

Leu Ser Gln Lys Tyr Arg Val Arg Val Arg Tyr Ala Thr Ser Val Ser
545 550 555 560

Gly Leu Phe Asn Val Phe Ile Asn Asp Glu Ile Ala Leu Gln Lys Asn
565 570 575

Phe Gln Ser Thr Val Glu Thr Ile Gly Glu Gly Lys Asp Leu Thr Tyr
580 585 590

Gly Ser Phe Gly Tyr Ile Glu Tyr Ser Thr Thr Ile Gln Phe Pro Asn
595 600 605

Glu His Pro Lys Ile Thr Leu His Leu Asn His Leu Ser Asn Asn Ser
610 615 620

Pro Phe Tyr Val Asp Ser Ile Glu Phe Ile Pro Val Asp Val Asn Tyr
625 630 635 640

Asp Glu Lys Glu Lys Leu Glu Lys Ala Gln Lys Ala Val Asn Thr Leu
645 650 655

Phe Thr Glu Gly Arg Asn Ala Leu Gln Lys Tyr Val Thr Asp Tyr Lys
660 665 670

Val Asp Gln Val Ser Ile Leu Val Asp Cys Ile Ser Gly Asp Leu Tyr
675 680 685

Pro Asn Glu Lys Arg Glu Leu Gln Asn Leu Val Lys Tyr Ala Lys Arg
690 695 700

Leu Ser Tyr Ser Arg Asn Leu Leu Leu Asp Pro Thr Phe Asp Ser Ile
705 710 715 720

Asn Ser Ser Glu Glu Asn Gly Trp Tyr Gly Ser Asn Gly Ile Val Ile
725 730 735

Gly Asn Gly Asp Phe Val Phe Lys Gly Asn Tyr Leu Ile Phe Ser Gly
740 745 750

Thr Asn Asp Thr Gln Tyr Pro Thr Tyr Leu Tyr Gln Lys Ile Asp Glu
755 760 765

Ser Lys Leu Lys Glu Tyr Ser Arg Tyr Lys Leu Lys Gly Phe Ile Glu
770 775 780

Ser Ser Gln Asp Leu Glu Ala Tyr Val Ile Arg Tyr Asp Ala Lys His
785 790 795 800

Arg Thr Leu Asp Val Ser Asp Asn Leu Leu Pro Asp Xaa Leu Pro Glu
805 810 815

Asn Thr Cys Gly Glu Pro Asn Arg Cys Ala Ala Gln Gln Tyr Leu Asp
820 825 830

Glu Asn Pro Ser Ser Glu Cys Ser Ser Met Gln Asp Gly Ile Leu Ser
835 840 845

Asp Ser His Ser Phe Ser Leu Asn Ile Asp Thr Gly Ser Ile Asn His
850 855 860

Asn Glu Asn Leu Gly Ile Trp Val Leu Phe Lys Ile Ser Thr Leu Glu
865 870 875 880

Gly Tyr Ala Lys Phe Gly Asn Leu Glu Val Ile Glu Asp Gly Pro Val
885 890 895

Ile Gly Glu Ala Leu Ala Arg Val Lys Arg Gln Glu Thr Lys Trp Arg
900 905 910

-continued

| | | | | | | | | | | | | | | | |
|---|---|---|---|---|---|---|---|---|---|---|---|---|---|---|---|
| Asn | Lys | Leu | Ala | Gln | Met | Thr | Thr | Glu | Thr | Gln | Ala | Ile | Tyr | Thr | Arg |
| | | 915 | | | | | 920 | | | | | 925 | | | |
| Ala | Lys | Gln | Ala | Leu | Asp | Asn | Leu | Phe | Ala | Asn | Ala | Gln | Asp | Ser | His |
| | 930 | | | | | 935 | | | | | 940 | | | | |
| Leu | Lys | Ile | Asp | Val | Thr | Phe | Ala | Glu | Ile | Ala | Ala | Ala | Arg | Lys | Ile |
| 945 | | | | | 950 | | | | | 955 | | | | | 960 |
| Val | Gln | Ser | Ile | Arg | Glu | Xaa | Xaa | Met | Ser | Trp | Leu | Ser | Val | Val | Pro |
| | | | | 965 | | | | | 970 | | | | | 975 | |
| Gly | Val | Asn | His | Pro | Ile | Phe | Thr | Glu | Leu | Ser | Gly | Arg | Val | Gln | Arg |
| | | | 980 | | | | | 985 | | | | | 990 | | |
| Ala | Phe | Gln | Leu | Tyr | Asp | Val | Arg | Asn | Val | Val | Arg | Asn | Gly | Arg | Phe |
| | | 995 | | | | | 1000 | | | | | 1005 | | | |
| Leu | Asn | Gly | Leu | Ser | Asp | Trp | Ile | Val | Thr | Ser | Asp | Val | Asn | Val | Gln |
| | 1010 | | | | | 1015 | | | | | 1020 | | | | |
| Glu | Glu | Asn | Gly | Asn | Asn | Val | Leu | Val | Leu | Asn | Asn | Trp | Asp | Ala | Gln |
| 1025 | | | | | 1030 | | | | | 1035 | | | | | 1040 |
| Val | Leu | Arg | Asn | Val | Lys | Leu | Tyr | Gln | Asp | Arg | Gly | Tyr | Val | Leu | Arg |
| | | | | 1045 | | | | | 1050 | | | | | 1055 | |
| Val | Thr | Ala | Arg | Lys | Ile | Gly | Ile | Gly | Glu | Gly | Tyr | Ile | Thr | Ile | Thr |
| | | | 1060 | | | | | 1065 | | | | | 1070 | | |
| Asp | Glu | Glu | Gly | His | Thr | Asp | Gln | Leu | Arg | Phe | Thr | Ala | Cys | Glu | Glu |
| | | 1075 | | | | | 1080 | | | | | 1085 | | | |
| Ile | Asp | Ala | Ser | Asn | Ala | Phe | Ile | Ser | Gly | Tyr | Ile | Thr | Lys | Glu | Leu |
| | 1090 | | | | | 1095 | | | | | 1100 | | | | |
| Glu | Phe | Phe | Pro | Asp | Thr | Glu | Lys | Val | His | Ile | Glu | Ile | Gly | Glu | Thr |
| 1105 | | | | | 1110 | | | | | 1115 | | | | | 1120 |
| Glu | Gly | Ile | Phe | Leu | Val | Glu | Ser | Ile | Glu | Leu | Phe | Leu | Met | Glu | Glu |
| | | | | 1125 | | | | | 1130 | | | | | 1135 | |
| Leu | Cys | | | | | | | | | | | | | | |

COLEOPTERAN-ACTIVE *BACILLUS THURINGIENSIS* ISOLATES AND GENES ENCODING COLEOPTERAN-ACTIVE TOXINS

CROSS-REFERENCE TO A RELATED APPLICATION

This is a continuation-in-part of copending application Ser. No. 07/788,638, filed Nov. 6, 1991.

BACKGROUND OF THE INVENTION

The soil microbe *Bacillus thuringiensis* (*B.t.*) is a Gram-positive, spore-forming bacterium characterized by parasporal crystalline protein inclusions. These often appear microscopically as distinctively shaped crystals. The proteins are highly toxic to pests and specific in their activity. Certain *B.t.* toxin genes have been isolated and sequenced, and recombinant DNA-based *B.t.* products produced and approved. In addition, with the use of genetic engineering techniques, new approaches for delivering *B.t.* endotoxins to agricultural environments are under development, including the use of plants genetically engineered with endotoxin genes for insect resistance and the use of stabilized intact microbial cells as *B.t.* endotoxin delivery vehicles (Gaertner, F. H., L. Kim [1988] TIBTECH 6:S4-S7). Thus, isolated *B.t.* endotoxin genes are becoming commercially valuable.

*Bacillus thuringiensis* produces a proteinaceous paraspore or crystal which is toxic upon ingestion by a susceptible insect host. Over most of the past 30 years, commercial use of *B.t.* pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystal called a delta endotoxin which is toxic to the larvae of a number of lepidopteran insects.

In recent years, however, investigators have discovered *B.t.* pesticides with specificities for a much broader range of pests. For example, other species of *B.t.*, namely *israelensis* and *san diego* (a.k.a. *B.t. tenebrionis*), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255). See also Couch, T. L. (1980) "Mosquito Pathogenicity of *Bacillus thuringiensis* var. *israelensi*," *Developments in Industrial Microbiology* 22:61–76; Beegle, C. C., (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang. Ent.* 96:500–508, describe a *B.t.* isolate named *Bacillus thuringiensis* var. *tenebrionis*, which is reportedly active against two beetles in the order Coleoptera. These are the Colorado potato beetle, *Leptinotarsa decemlineata*, and *Agelastica alni*.

Recently, many new subspecies of *B.t.* have been identified, and many genes responsible for active δ-endotoxin proteins have been isolated (Höfte, H., H. R. Whiteley [1989]*Microbiological Reviews* 52(2):242–255). Höfte and Whiteley classified 42 *B.t.* crystal protein genes into 14 distinct genes, grouped into 4 major classes based on amino-acid sequence and host range.

The classes were CryI (Lepidoptera-specific), CryII (Lepidoptera-and Diptera-specific), CryIII (Coleoptera-specific), and CryIV (Diptera-specific). The discovery of strains specifically toxic to protozoan pathogens, animal-parasitic liver flukes (Trematoda), or mites (Acari) has broadened the potential *B.t.* product spectrum even further (see Feitelson, J. S., J. Payne, L. Kim [1992]*Bio/Technology* 10:271–275). With activities against unique targets, these novel strains retain their very high biological specificity; nontarget organisms remain unaffected. The availability of a large number of diverse *B.t.* toxins may also enable farmers to adopt product-use strategies that minimize the risk that *B.t.*-resistant pests will arise.

The cloning and expression of a *B.t.* crystal protein gene in *Escherichia coli* has been described in the published literature (see, for example, Schnepf, H.E., H. R. Whitely [1981] *Proc. Natl. Acad. Sci. USA* 78:2893–2897). U.S. Pat. No. 4,448,885 and U.S. Pat. No. 4,467,036 both disclose the expression of *B.t.* crystal protein in *E. coli*. U.S. Pat. No. 4,853,331 discloses *B. thuringiensis* strain *san diego* (a.k.a. *B.t. tenebrionis*) which can be used to control coleopteran pests in various environments.

BRIEF SUMMARY OF THE INVENTION

The subject invention concerns the discovery that certain known and publicly available strains of *Bacillus thuringiensis* (B.t.) are active against coleopteran pests. This is a surprising discovery since these B.t. microbes were not known to have any insecticidal properties.

The microbes of the subject invention were obtained from the Howard Dalmage collection held by the NRRL culture repository in Peoria, Ill. and are designated *B.t.* HD511, *B.t.* HD867, and *B.t.* HD1011. These microbes, and variants of these microbes, as well as genes and toxins obtainable therefrom, can be used to control coleopteran pests. The procedures for using these microbes are similar to known procedures for using *B.t.* microbes to control coleopteran pests.

The subject invention also includes variants of *B.t.* microbes which have substantially the same pesticidal properties as the exemplified isolates. These variants would include, for example, mutants. Procedures for making mutants are well known in the microbiological art. Ultraviolet light and nitrosoguanidine are used extensively toward this end.

Further, the invention also includes the treatment of substantially intact *B.t.* cells, and recombinant cells containing a gene of the invention, to prolong the pesticidal activity when the substantially intact cells are applied to the environment of a target pest. Such treatment can be by chemical or physical means, or a combination of chemical or physical means, so long as the technique does not deleteriously affect the properties of the pesticide, nor diminish the cellular capability in protecting the pesticide. The treated cell acts as a protective coating for the pesticidal toxin. The toxin becomes available to act as such upon ingestion by a target insect.

Disclosed herein are specific toxins, and nucleotide sequences encoding these toxins, obtainable from the exemplified isolates. Advantageously, these nucleotide sequences can be used to transform other microbes or plants to create insecticidal compositions and plants.

BRIEF DESCRIPTION OF THE SEQUENCES

SEQ ID NO. 1 is the nucleotide sequence encoding toxin HD511.

SEQ ID NO. 2 is the amino acid sequence of toxin HD511.

SEQ ID NO. 3 is the nucleotide sequence encoding toxin HD867.

SEQ ID NO. 4 is the amino acid sequence of toxin HD867.

DETAILED DISCLOSURE OF THE INVENTION

A summary of the characteristics of the *B. thuringiensis* microbes of the subject invention is shown in Table 1.

TABLE 1

A comparison of the novel coleopteran-active strains with B.t.s.d.

| Strain | Crystal Type | Approx. Molecular Weight of Protein* | Serotype |
|---|---|---|---|
| HD511 | Bipyramid | 130, 143 | 15, dakota |
| HD867 | Bipyramid | 130 | 18, kumamotoensis |
| HD1011 | Multiple amorphic | 130, 140 | 20a20c, pondicheriensis |

*as shown on a standard polyacrylamide gel.

The cultures disclosed in this application are on deposit in the Agricultural Research Service Patent Culture Collection (NRRL), Northern Regional Research Center, 1815 North University Street, Peoria, Ill. 61604, USA.

In a preferred embodiment, the nucleotide sequence information provided herein can be used to make primers which, when using standard PCR procedures, can be used to obtain the desirable genes from the disclosed isolates. These procedures are well known and commonly used in this art. Alternatively, synthetic genes, or portions thereof, can be made using a "gene machine" and the sequence information provided herein.

The subject invention pertains not only to the specific genes and toxins exemplified herein, but also to genes and toxins obtainable from variants of the disclosed isolates. These variants would have essentially the same coleopteran activity as the exemplified isolates. Furthermore, using the DNA and amino acid sequence provided herein, a person skilled in the art could readily construct fragments or mutations of the genes and toxins disclosed herein. These fragments and mutations, which retain the coleopteran activity of the exemplified toxins, would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or similar, toxins. These DNA sequences are within the scope of the subject invention. As used herein, reference to "essentially the same" sequence refers to sequences which have amino acid substitutions, deletions, additions, or insertions which do not materially affect coleopteran activity. Fragments retaining coleopteran activity are also included in this definition.

The coleopteran-active toxin genes of the subject invention can be isolated by known procedures and can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of coleopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the *B.t.* toxin.

Where the *B.t.* toxin gene is introduced via a suitable vector into a microbial host, and said host is applied to the environment in a living state, it is important that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus*and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

A wide variety of ways are available for introducing the *B.t.* gene expressing the toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression begins. Other techniques may employ a specific nutrient medium in the laboratory, which inhibits the expression of the toxin, where the nutrient medium in the environment allows for expression of the toxin. For translational initiation, a ribosomal binding site and an initiation codon will be present.

Various manipulations may be employed for enhancing the expression of the messenger, particularly by using an active promoter, as well as by employing sequences, which enhance the stability of the messenger RNA. The initiation and translational termination region will involve stop codon(s), a terminator region, and optionally, a polyadenylation signal.

In the direction of transcription, namely in the 5′ or 3′ direction of the coding or sense sequence, the construct can involve the transcriptional regulatory region, if any, and the promoter, where the regulatory region may be either 5′ or 3′ of the promoter, the ribosomal binding site, the initiation codon, the structural gene having an open reading frame in phase with the initiation codon, the stop condon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et. al. (1982) *J. Bacteriol.* 150:6069, and Bagdasarian et. al. (1981) *Gene* 16:237, and U.S. Pat. Nos. 4,356,270, 4,362,817, and 4,371,625.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the tac promoter, and the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

The *B.t.* gene can be introduced between the transcriptional and translational initiation region and the transcriptional and translational termination region, so as to be under the regulatory control of the initiation region. This construct can be included in a plasmid, which could include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L. [1967] *Animal Tissue Techniques*, W. H. Freeman and Company); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis*, and the like.

The cellular host containing the *B.t.* gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least about 1% by weight and may be about 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the coleopteran pest(s), e.g., plants, soil or water, by spraying, dusting, sprinkling, or the like.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing *B.t.* Microbes

A subculture of a *B.t.* microbe, as disclosed herein, can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |

-continued

| |
|---|
| pH 7.2 |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The *B.t.* spores and crystals, obtained in the above fermentation, can be isolated by procedures well known in the art. A frequently-used procedure is to subject the harvested fermentation broth to separation techniques, e.g., centrifugation.

EXAMPLE 2

Testing of *B.t.* Microbes Spores and Crystals

The *B.t.* strains were tested against *Leptinotarsa rubiginosa*, a surrogate for *Leptinotarsa decemlineata*, the Colorado potato beetle.

The bioassay was performed on two different *Bacillus thuringiensis* preparations. (1) The spore/crystal pellet was resuspended in water. (2) The spore/crystal pellet was treated with 0.1M $Na_2CO_3$, pH 11.5, with 0.5% 2-mercaptoethanol for two hours at room temperature. Prep #2 was dialyzed against 0.1M Tris, pH 8, for three hours with three changes of 15 times the sample volume. Prep #1 and Prep #2 contained equal amounts of active ingredient.

Leaves were dipped in the *B.t.* preparations, and first instar larvae were placed on the leaves. The larvae were incubated at 25° C. for 4 days before mortality was determined.

TABLE 2

| | Percent Mortality | |
|---|---|---|
| Strain | Prep #1 | Prep #2 |
| HD511 | 52% | 92% |
| HD867 | 92% | 100% |
| HD1011 | 36% | 92% |
| Control | 0% | 0% |

EXAMPLE 3

Insertion of Toxin Gene Into Plants

One aspect of the subject invention is the transformation of plants with genes encoding a coleopteran toxin. The transformed plants are resistant to attack by coleopterans.

Genes encoding lepidopteran-active toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the *B.t.* toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1-46; and An et al. (1985) *EMBO J.* 4:277-287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in E. coli and in agrobacteria. They comprise a selection marker gene and a linker or polylinker which are framed by the right and left T-DNA border regions. They can be transformed directly into agrobacteria (Holsters et al. [1978] *Mol. Gen. Genet.* 163:181-187). The agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

EXAMPLE 4

Cloning of Novel *B.t.* Genes Into Insect Viruses

A number of viruses are known to infect insects. These viruses include, for example, baculoviruses and entomopoxviruses. In one embodiment of the subject invention, lepidopteran-active genes, as described herein, can be placed with the genome of the insect virus, thus enhancing the pathogenicity of the virus. Methods for constructing insect viruses which comprise *B.t.* toxin genes are well known and readily practiced by those skilled in the art. These procedures are described, for example, in Merryweather et al. (Merryweather, A. T., U. Weyer, M. P. G. Harris, M. Hirst, T. Booth, R. D. Possee [1990] *J. Gen. Virol.* 71:1535–1544) and Martens et al. (Martens, J. W. M., G. Honee, D. Zuidema, J. W. M. van Lent, B. Visser, J. M. Vlak [1990] *Appl. Environmental Microbiol.* 56(9):2764–2770).

We claim:

1. An isolated nucleotide sequence comprising DNA encoding a *Bacillus thuringiensis* toxin active against coleopteran pests, wherein said DNA encodes a toxin consisting essentially of the amino acid sequence of SEQ ID NO. 2 or SEQ ID NO. 4, or portions thereof having activity against coleopteran pests.

2. The isolated nucleotide sequence, according to claim 1, wherein said DNA encodes a *Bacillus thuringiensis* toxin having essentially the amino acid sequence shown in SEQ ID NO. 2.

3. The isolated nucleotide sequence, according to claim 2, wherein said DNA has essentially the sequence shown in SEQ ID NO. 1.

4. The isolated nucleotide sequence, according to claim 1, wherein said DNA encodes a *Bacillus thuringiensis* toxin having essentially the amino acid sequence shown in SEQ ID NO. 4.

5. The isolated nucleotide sequence, according to claim 2, wherein said DNA has essentially the sequence shown in SEQ ID NO. 3.

6. A bacterial host transformed to express a heterologous *Bacillus thuringiensis* toxin active against coleopteran pests wherein said toxin is encoded by DNA which encodes a toxin consisting essentially of the amino acid sequence of SEQ ID NO. 2 or SEQ ID NO. 4, or portions thereof having activity against coleopteran pests.

7. The bacterial host, according to claim 6, which is a species of Pseudomonas, Azotobacter, Erwinia, Serratia, Klebsiella, Rhizobium, Bacillus, Streptomyces, Rhodopseudomonas, Methylophilius, Agrobacterium, Acetobacter, or Alcaligenes.

8. The bacterial host, according to claim 7, wherein said bacterium is pigmented and phylloplane adherent.

9. The bacterial host, according to claim 6, wherein said host is transformed with an isolated nucleotide sequence comprising DNA encoding a toxin having an amino acid sequence which essentially the amino acid sequence shown in SEQ ID NO. 2.

10. The bacterial host, according to claim 6, wherein said host is transformed with an isolated nucleotide sequence comprising DNA encoding a toxin having an amino acid sequence which is essentially the amino acid sequence shown in SEQ ID NO. 4.

11. Treated, substantially intact unicellular microorganism cells containing an intracellular toxin, which toxin is a result of expression of a heterologous nucleotide sequence which encodes a polypeptide toxin active against coleopteran pests wherein said nucleotide sequence encodes a toxin wherein said toxin comprises an amino acid sequence which is essentially the amino acid sequence of SEQ ID NO. 2 or SEQ ID NO. 4, or portions thereof having activity against coleopteran pests; wherein said cells are treated under conditions which prolong the insecticidal activity when said cells are applied to the environment of a target insect.

* * * * *

UNITED STATES PATENT AND TRADEMARK OFFICE

CERTIFICATE OF CORRECTION

PATENT NO. : 5,286,486

DATED : Feb. 15, 1994

INVENTOR(S) : Jewel Payne, et al

It is certified that error appears in the above-indentified patent and that said Letters Patent is hereby corrected as shown below:

Column 4, line 50: Delete "*entrophus*and" and insert --*entrophus*, and--.

Column 5, line 26: Delete "5′ or 3′" and insert --5′ to 3′--.

Signed and Sealed this

Sixth Day of September, 1994

Attest:

BRUCE LEHMAN

*Attesting Officer*

*Commissioner of Patents and Trademarks*